United States Patent
Tsai et al.

(10) Patent No.: US 9,482,518 B2
(45) Date of Patent: Nov. 1, 2016

(54) SYSTEMS AND METHODS FOR SEMICONDUCTOR DEVICE PROCESS DETERMINATION USING REFLECTIVITY MEASUREMENT

(71) Applicant: TAIWAN SEMICONDUCTOR MANUFACTURING COMPANY, LTD., Hsin-Chu (TW)

(72) Inventors: Chun Hsiung Tsai, Hsinchu County (TW); Sheng-Wen Yu, New Taipei (TW); De-Wei Yu, Ping-Tung (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 0 days.

(21) Appl. No.: 14/536,298

(22) Filed: Nov. 7, 2014

(65) Prior Publication Data

US 2015/0292868 A1    Oct. 15, 2015

Related U.S. Application Data

(60) Continuation-in-part of application No. 14/263,693, filed on Apr. 28, 2014, now Pat. No. 8,883,522, which is a division of application No. 13/491,252, filed on Jun. 7, 2012, now Pat. No. 8,753,904.

(51) Int. Cl.
| | |
|---|---|
| *H01L 21/00* | (2006.01) |
| *G01B 11/14* | (2006.01) |
| *G01N 21/55* | (2014.01) |
| *H01L 21/66* | (2006.01) |
| *H01L 21/02* | (2006.01) |
| *H01L 21/324* | (2006.01) |

(52) U.S. Cl.
CPC .............. *G01B 11/14* (2013.01); *G01N 21/55* (2013.01); *H01L 21/02636* (2013.01); *H01L 21/324* (2013.01); *H01L 22/12* (2013.01); *H01L 22/20* (2013.01); *G01N 2021/551* (2013.01); *G01N 2021/555* (2013.01); *G01N 2021/557* (2013.01); *G01N 2201/061* (2013.01)

(58) Field of Classification Search
None
See application file for complete search history.

(56) References Cited

U.S. PATENT DOCUMENTS

| | | |
|---|---|---|
| 5,561,088 A | 10/1996 | Sameshima |
| 6,333,485 B1 | 12/2001 | Haight et al. |
| 6,403,396 B1 | 6/2002 | Gudesen et al. |
| 6,432,739 B1 | 8/2002 | Gudesen et al. |
| 6,656,749 B1 | 12/2003 | Paton et al. |
| 6,727,108 B2 | 4/2004 | Eriguchi et al. |
| 6,776,806 B2 | 8/2004 | Gudesen et al. |
| 6,818,864 B2 | 11/2004 | Ptak |
| 7,098,155 B2 | 8/2006 | Talwar et al. |

(Continued)

OTHER PUBLICATIONS

Metrology of epitaxial thin-flms by advanced HRXRD and XRR by Ryan et al., Published Jun. 1, 2011.*

(Continued)

*Primary Examiner* — Evren Seven
(74) *Attorney, Agent, or Firm* — Haynes and Boone, LLP (57) ABSTRACT

Methods and systems that include receiving a plurality of reflectivity measurements on a semiconductor wafer. A reflectivity map is generated based on the received plurality of reflectivity measurements. The generated reflectivity map is used to determine a process parameter of an epitaxial growth process using the reflectivity map. In an embodiment, the process parameter is a power setting (heating) of a lamp of a CVD epitaxy tool.

20 Claims, 6 Drawing Sheets

(56) References Cited

U.S. PATENT DOCUMENTS

| | | |
|---|---|---|
| 7,148,159 B2 | 12/2006 | Talwar et al. |
| 7,262,864 B1 | 8/2007 | Markle et al. |
| 7,305,651 B2 | 12/2007 | Cao |
| 7,348,192 B2 | 3/2008 | Mikami |
| 7,494,942 B2 | 2/2009 | Talwar et al. |
| 7,623,978 B2 | 11/2009 | Lally et al. |
| 7,820,531 B2 | 10/2010 | Matsunobu et al. |
| 7,879,741 B2 | 2/2011 | Talwar et al. |
| 7,935,585 B2 | 5/2011 | Sato et al. |
| 8,232,114 B2 | 7/2012 | Lin et al. |
| 8,753,904 B2 | 6/2014 | Tsai |
| 2005/0112788 A1 | 5/2005 | Borden et al. |
| 2005/0200850 A1 | 9/2005 | Borden et al. |
| 2007/0020784 A1 | 1/2007 | Timans |
| 2007/0105247 A1 | 5/2007 | Mauersberger et al. |
| 2007/0217289 A1 | 9/2007 | Watabe et al. |
| 2010/0190274 A1 | 7/2010 | Lin et al. |
| 2012/0015459 A1 | 1/2012 | Tsai et al. |
| 2012/0021539 A1 | 1/2012 | Allenic et al. |
| 2013/0330844 A1 | 12/2013 | Hawryluk et al. |
| 2014/0233043 A1 | 8/2014 | Tsai et al. |

OTHER PUBLICATIONS

P.J. Timans; "A Short History of Pattern Effects in Thermal Processing / Rapid Thermal Processing and Beyond: Applications in Semiconductor Processing;" Materials Science Forum vols. 573-574 (Mar. 24, 2008), pp. 355-374, www.scientific.net.

Andrew J. Newman, P.S. Krishnaprasad, Sam Ponczak and Paul Brabant, "Modeling and Model Reduction for Control and Optimization of Epitaxial Growth in a Commercial Rapid Thermal Chemical Vapor Deposition Reactor," Technical Research Report, T.R. 98-45, 63 Pages; Institute for Systems Research, http://www.isr.umd.edu.

\* cited by examiner

SYSTEMS AND METHODS FOR SEMICONDUCTOR DEVICE PROCESS DETERMINATION USING REFLECTIVITY MEASUREMENT

CROSS REFERENCE

This application is a continuation-in-part of U.S. patent application Ser. No. 14/263,693 filed on Apr. 28, 2014, entitled "System For Semiconductor Device Characterization Using Reflectivity Measurement," now U.S. Pat. No. 8,883,552, issued on Nov. 11, 2014, which in turn is a divisional of U.S. patent application Ser. No. 13/491,252 filed on Jun. 7, 2012, entitled "Method and System for Semiconductor Device Pattern Loading Effect Characterization," now U.S. Pat. No. 8,753,904, issued on Jun. 17, 2014, the disclosures of which are incorporated herein by reference.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process has decreased. This scaling down process generally provides benefits by increasing production efficiency and lowering associated costs. Such scaling down has also increased the complexity of processing and manufacturing ICs and, for these advances to be realized, similar developments in IC processing and manufacturing are needed.

One IC process typically performed during semiconductor device fabrication is an anneal. For example, an anneal may be used to drive-in dopants to provide a suitable dopant profile. Another IC process is that of epitaxial growth on a substrate. One challenge with the increasing complexity of semiconductor devices is the presence of a loading effect, also referred to as a pattern loading effect (PLE) during processes. The pattern loading effect phenomenon derives from differences in radiant energy absorption in different areas of a semiconductor device or die on account of the different patterning (e.g., pattern density, aspect ratio of features, composition/reflectivity of features, etc.). In conventional processing the effects on semiconductor device performance from the PLE is characterized during electrical test. This has its disadvantages in efficiency and effectiveness of the characterization.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Various features may be arbitrarily drawn in different scales for simplicity and clarity. The term characterization as used herein includes, but is not limited to, an analysis of a semiconductor device, semiconductor device design, the analysis and/or determination of various process parameters, analysis and/or determination of design elements or layout, disposition of material (e.g., product, device, wafer, lot), analysis and/or determination of process technique to be used, and/or other functions.

During semiconductor device fabrication, a thin layer of semiconductor material may be doped to alter the electrical characteristics of the material. Generally, doping is the process of implanting ions into the semiconductor material and may be performed by an ion implant process wherein the semiconductor layer is bombarded with N-type and/or P-type ions or by an in situ process wherein ions are introduced as the semiconductor layer is being formed.

After the doping process, an annealing process is typically performed to activate the implanted ions (e.g., N-type and/or P-type ions). When performing the annealing procedure, however, it has been found that the individual dies of a wafer may not heat evenly, or specifically a different amount of heat may be absorbed at different regions of a die and/or wafer. In some embodiments, the die may exhibit a significant amount of temperature variation across the die. The variations in heat absorbed may stem from differences in doping level, pattern density, pattern configuration, pattern aspect ratio, reflectivity of layers, and/or other variations across a die. This is referred to herein as a pattern loading effect (PLE). This pattern loading effect and resultant temperature differences may result in the various semiconductor devices, e.g., transistors, resistors, capacitors, and the like, on the same die to exhibit different electrical characteristics.

For example, when a first region, e.g., edges of a die, are heated to a significantly lower temperature than a second region, e.g., the center of the die, the dopants in the second region may not be sufficiently activated resulting in increased resistance and greater circuit delays as compared to the first region. As another example, when a first region is heated to a lower temperature than the second region, the epitaxial growth rate may be different between the two regions. As a result, the various semiconductor devices or portions of the IC may have different electrical characteristics based upon the position on the die.

Figure 1:
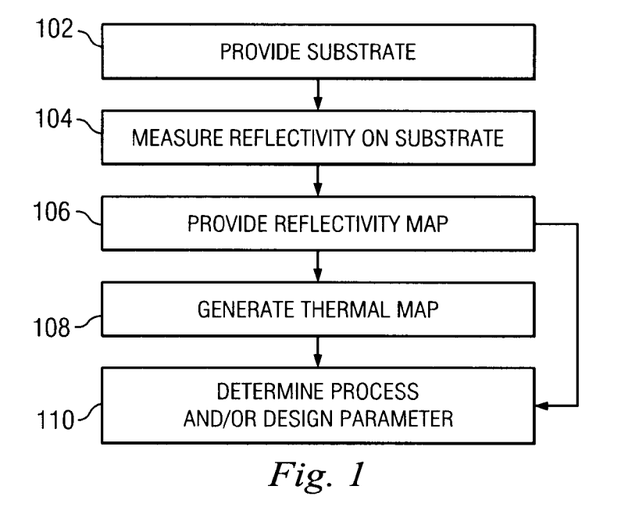
FIG. 1 is a flow chart illustrating an embodiment of a method of characterization according to one or more aspects of the present disclosure.

Referring now to FIG. 1, illustrated is a method 100 of characterizing a wafer and/or die including determining a pattern loading effect. The method 100 may be used to determine, for a given wafer, die or design—a device performance parameter, a suitable process technique for its fabrication, and/or a determination of the suitability of a layout provided on the wafer or die.

The method 100 begins at block 102 where a substrate is provided. In an embodiment, the substrate is a semiconductor wafer. The wafer may be a silicon wafer. The substrate may also include other elementary semiconductors such as germanium and diamond. Alternatively, the substrate may include a compound semiconductor and/or an alloy semiconductor. Further, the substrate may optionally include an epitaxial layer (epi layer), may be strained for performance enhancement, may include a silicon-on-insulator (SOI) structure, and/or have other suitable enhancement features. The wafer may include a plurality of die formed thereon.

The die may include any number of semiconductor devices, such as field effect transistors (FETs), capacitors, resistors, conductive interconnects, and/or other suitable devices. The die may include various doped regions or regions of the substrate (including layers on semiconductor wafer) with suitable N-type or P-type dopants (impurities). Exemplary regions include active regions on which MOS devices can be formed; the active regions may be doped to form well regions. The doped regions, including but not limited to active regions, may vary in dimension, dopant level, configuration, and/or other properties. The boundaries of the active regions may be defined by isolation structures such as shallow trench isolation (STI) features.

The die may also include any plurality of layers formed on a base substrate including conductive layers, insulating layers, masking layers, antireflective coatings, etch stop layers, gate layers, interconnection layers, and/or other features. These layers may form features (e.g., gate structures, conductive capacitor plates, interconnect lines, source/drain regions, isolation regions) of varying dimensions (e.g., height and widths). These layers may also form regions on the die having different pattern densities.

Figure 2:
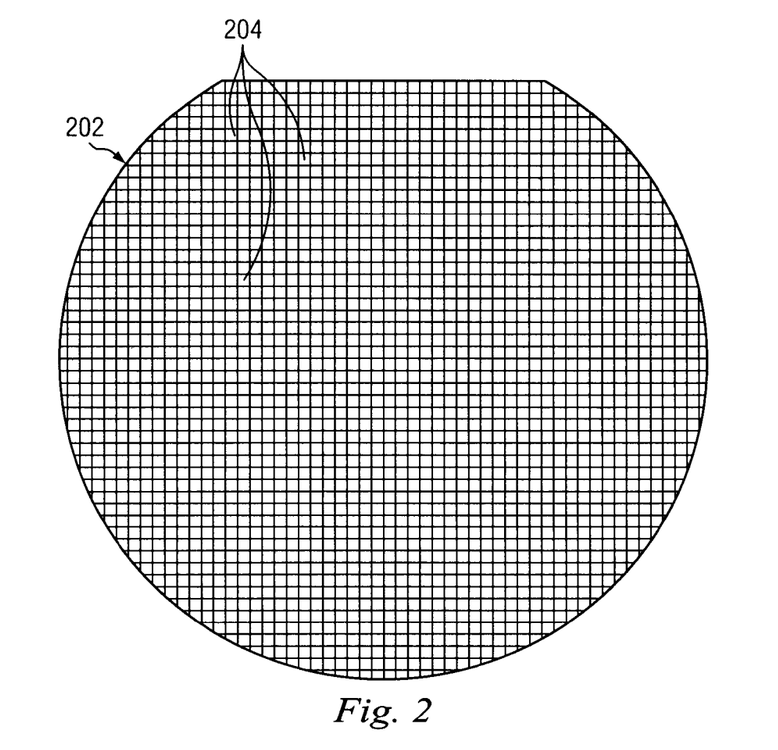
FIG. 2 is a top view of an embodiment of a wafer.

In an embodiment, the dies may be representative of a single semiconductor device product. In another embodiment, the dies may be used to form any number of different semiconductor device products. In other words, the dies of a wafer may be associated with different designs or a common design. For example, a first plurality of dies of the wafer may be a first semiconductor device product or have a first design; a second plurality of dies on the same wafer may be a second semiconductor device product or have a second design. Referring to the example of FIG. 2, a wafer 202 is illustrated having a plurality of dies 204. One or more die 204 of the wafer 202 may have a different intra-die pattern loading effect. In other embodiments, one or more die 204 exhibit a substantially similar intra-die pattern loading effect.

The method 100 then proceeds to block 104 where a reflectivity is measured for the substrate. The reflectivity of the substrate, and/or a die formed thereon, may be dependent upon the materials present, the pattern density of the devices, e.g., transistors, resistors, capacitors, and/or other suitable factors. The reflectivity measured includes the amount (e.g., intensity) of radiation (light) reflected from a radiation beam incident the substrate.

In an embodiment, the reflectivity measurement of the substrate is performed using a radiation source that has a relativity short wavelength such as, for example, a source providing a radiation beam having a wavelength between approximately 200 nanometers (nm) and approximately 750 nm. Thus, in an embodiment, a flash Xeon lamp is used as a light source. In an embodiment, the main distribution of the wavelength of the radiation (e.g., light) source is between approximately 300 nm and approximately 500 nm. This may provide a wavelength distribution of reflectivity measurement that covers the wavelength distribution of a radiation/light source, which is actually experienced by the substrate during an anneal process.

In an embodiment, the reflectivity measurement of the substrate may be performed using a light source that is from the visible light range. In an embodiment, the reflectivity measurement is from a light source that is in the infrared (IR) range. For example, the light source may provide a radiation beam having a wavelength between approximately 400 nanometers and approximately 5 microns. In an embodiment, the selection of the wavelength and/or type of light source is dependent upon the process parameter to be determined using the method 100.

The reflectivity measurement may include a scan of the substrate. The scan may be a full-wafer scan, or a scan of a representative sample of regions (e.g., die) on the device. In an embodiment, a spot size of approximately 3 µm is used for the scan. In a further embodiment, a stepping distance of approximately 50 µm or greater is used. These scan parameters are by way of example only. The reflectivity measurement or scan may provide a two-dimensional reflectivity map corresponding to the substrate. The reflectivity map may include a reflectivity measurement for one or more points on the substrate.

Figure 3:
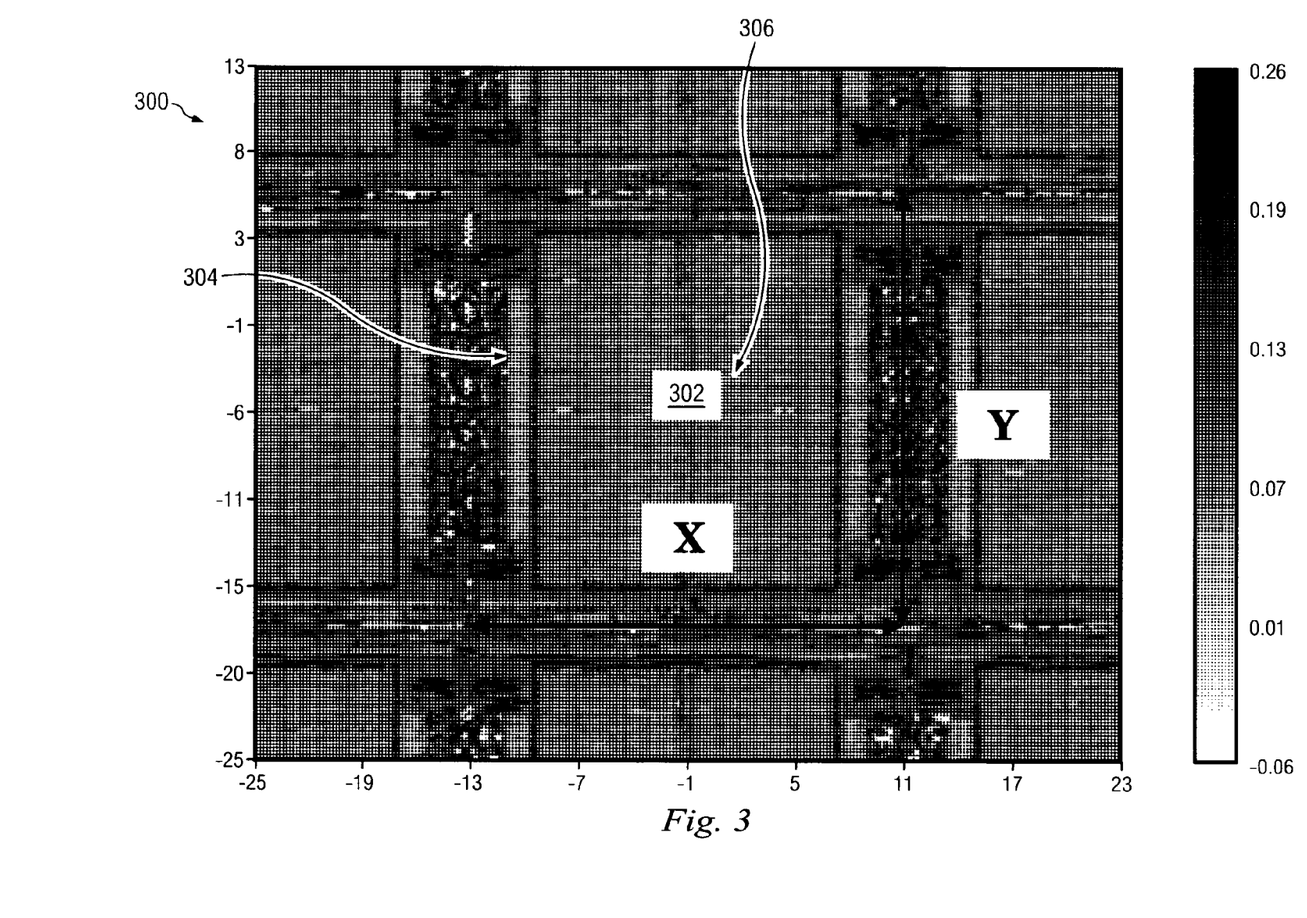
FIG. 3 is an embodiment of a reflectivity map such as generated during one or more steps of the method of FIG. 1.

An exemplary reflectivity map 300 is illustrated in FIG. 3. Though the reflectivity map 300 illustrates a portion of a wafer (e.g., approximately 9 die), any size of area may be used in the scan and/or provided in the reflectivity map. In an embodiment, the reflectivity map is representative of an entire substrate. In another embodiment, the reflectivity map is representative of one or more die on the substrate (e.g., map 300).

The reflectivity map 300 illustrates a plurality of dies including die 302. Die 302 has a dimension of X and Y. In an embodiment, X and Y may be approximately 2 centimeters (cm). However, any dimension is possible. In fact, one advantage of various embodiments of the present disclosure is that it can be used for any technology node or any sized/configuration of die. The reflectivity map 300 includes a value of intensity of a reflected radiation beam determined for a given point (or points) on a substrate. The reflectivity map 300 illustrates the die 302 has a relatively higher reflectivity at the edge-region 304 and a relatively lower reflectivity at the center-region 306. The reflectivity scale of the map 300 includes a low reflectivity (e.g., 0, 0.01) to higher relative reflectivity (e.g., 0.26).

In an embodiment, the method 100 proceeds to block 110 where the reflectivity map may be analyzed to determine a process parameter including, for example, determining a specific anneal technique to implement as described in further detail below, determining a device performance parameter (e.g., leakage, speed, etc including as described below with reference to a device performance parameter map), performing an evaluation of an associated design or layout (e.g., a determination of whether a modification layout to a design or layout is desired as described below), and/or other suitable characterization. Each of these characterizations is described in further detail below.

In an embodiment of the method 100 in block 110 the reflectivity may be analyzed to determine a process parameter such as a parameter of a chemical vapor deposition (CVD) epitaxial growth process, also referred to as CVD epitaxy. Exemplary process parameters that may be determined include those directed to a heating amount provided by one or more lamps of the CVD epitaxy tool such as, for example, the ratio of upper to lower lamp heating. This is described in further detail below. It is noted that the reflectivity map may be analyzed to meet any one of, combination of, or all of the aspects discussed herein. For example, the reflectivity map may be used to determine parameters/types of anneal processes, parameters associated with CVD epitaxy, generate thermal maps, and determine device performance (e.g., performance maps).

It is noted that reflectivity variation over a region (e.g., die) is an indication of the temperature variations over the same region. For example, there may be an inverse relationship between reflectivity and temperature: regions exhibiting a higher reflectivity are lower in temperature in comparison to regions exhibiting lower reflectivity. The reflectivity map may be used to predict device performance including intra- and/or inter-die variation. As described below, the analysis of the reflectivity map may be used to determine a configuration for an anneal process or other process such as a CVD epitaxy process.

For example, the higher the reflectivity, the greater the amount of the radiation energy of the heat source of the anneal may be reflected during the process. Thus, an appropriate anneal or epitaxial growth that allows for the pattern loading effect to be acceptable (within a given tolerance or margin) may be determined from the reflectivity map. An appropriate anneal may be one that may be performed without design modification to improve a PLE.

As an example, the pattern loading effect characterized and illustrated by the reflectivity may be used to address the pattern loading by modifying and/or selecting a configuration for a CVD epitaxy process such as determining a heat amount provided by various devices in the CVD epitaxy tool. As described above, the higher the reflectivity, the greater the amount of the radiation energy of the heat source of the epitaxial growth process may be reflected during the growth process. Thus, the heating of the wafer may affect the process outputs including epitaxial growth rate, epitaxial layer uniformity, epitaxial composition and the like. Thus, an appropriate heating may be desired in differ portions of a target substrate during the epitaxial growth such that epitaxial growth can be tailored for pattern loading effects providing desired growth, such as providing uniform growth of an epitaxial layer. In an embodiment, the heating is controlled by controlling a power of a lamp or lamp array as discussed below. As but one example, in a portion of the target substrate providing greater reflectivity, and thus, lower heat absorption of the substrate, additional heat (e.g., lamp power) may be desired to increase the heat absorption of the substrate to provide uniform temperature and/or epitaxial growth. Similarly, in another portion of the target substrate providing lower reflectivity, and thus, greater heat absorption of the substrate, decreased heat (e.g., lamp power) may be desired to decrease the heat absorption of the substrate at that region to provide uniform temperature and/or epitaxial growth. In an embodiment using dual side (upper and lower) heating process (e.g., for a thermal anneal, CVD, and/or epitaxy process), the front and back side heating or power ratio may determine how the pattern loading effects the process. For example, generally, the more power (heat) on the front side of a wafer (e.g., patterned wafer), the more thermal loading effect the wafer and process experience. In an embodiment, an approximately 20% frontside to 80% backside setting for power output may be determined. In other words, for the required heating, 20% is provided by power output from the frontside element or lamp and approximately 80% is provided by power output from the backside element or lamp. In an embodiment, an approximately 20% front to 80% backside setting for power output may be a baseline setting. If a reflectivity map illustrates a greater reflectivity variation (e.g., over a given spatial distance), then the power ratio may be modified from the base line. For example, the power of the front may be decreased from 20% and the backside power may be increased from 80%.

In some embodiments, the analysis of the reflectivity map may additionally or alternatively provide for a disposition of the design of a die (e.g., layout), a modification of the design of the die, a selection of an anneal process parameter, selection of an epitaxial CVD process parameter, a determination of a performance parameter for the device, and/or other suitable characterization. These analyses are described in greater detail below.

In an embodiment, the method 100 proceeds to block 108 where a thermal map is generated from the reflectivity map. The reflectivity map may be converted to a two-dimensional thermal map. By conducting an anneal of various blanket substrates (e.g., wafers) coating with films of individual and/or varying reflectivity (e.g., silicon nitride or an antireflective film), various temperatures can be detected on individual blanket wafers by inputting the same thermal budget. Therefore, the correlation between reflectivity and temperature can be determined. Thus, providing information for the reflectivity map to be converted into a thermal map.

Generally, in some embodiments, the thermal map may be generated using a model, experimental data, and/or other analysis techniques. For example, in an embodiment, a given percentage change in reflectivity provides a given temperature variation (e.g., as determined by a model). For example, a 10% reflectivity difference may provide an approximate 100 C variation. Thus, the reflectivity map may illustrate a reflectivity difference over a given distance of the substrate that can be correlated to provide a thermal map a region corresponding to that of the reflectivity map. The thermal map may be used to predict device performance including intra- and/or inter-die variation. For example, see the description directed to FIG. 4 below. The analysis of the thermal map may provide for a disposition of the design of a die (e.g., layout), a modification of the design of the die, a selection of an anneal process, a selection of a process parameter of a CVD epitaxy process, a selection of an anneal process parameter, a determination of a performance parameter for the device, and/or other suitable characterization.

Figure 4:
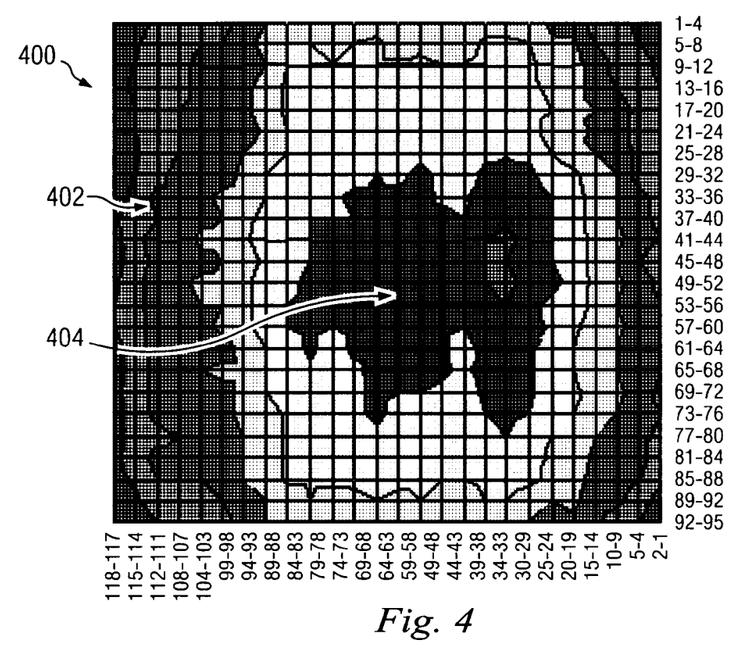
FIG. 4 is an embodiment of a thermal map such as generated during one or more steps of embodiments of the method of FIG. 1.

Referring to the example of FIG. 4, illustrated is a thermal map 400. The thermal map 400 illustrates a center region 404 and an edge region 402. The map 400 has a center-hot, edge-cool temperature profile. In an embodiment, a thermal map is generated having corresponding regions to an associated reflectivity map. In another embodiment, a one-to-one correlation between a thermal map and an associated reflectivity map is not required. For example, a correlation or model used to generate the thermal map may extrapolate one or more points, may have a reduction in the number of points calculated, may be over a reduced or increased area of a wafer, and/or other variations. In an embodiment, this center-hot, edge-cool temperature corresponds to a reflectivity map having a low reflectivity-center region and a high-reflectivity edge region (e.g., the reflectivity map 300). For example, the temperature and reflectivity are inversely related. The thermal map may include a thermal value at any number of points on a substrate or portion thereof. In some embodiments, generation of a thermal map is omitted.

The method 100 then proceeds to block 110 where a process, design, and/or device performance parameter is determined. The process, design, and/or device performance parameters may be determined using at least one of the reflectivity map, discussed above with reference to block 106 and the thermal map, discussed above with reference to block 108.

In an embodiment, a process parameter associated with the wafer is determined. The process parameter may be determined using the reflectivity measurement, the reflectivity map, and/or the thermal map.

In an embodiment, the process parameter may be a type of anneal technique to be performed, a duration of an anneal, a temperature of an anneal, and/or other suitable process parameters. In an embodiment, a determination of the process parameter includes determining a type of high temperature technique to perform, such as, for example, a rapid thermal anneal (RTA) (e.g., second RTA spike anneal), a millisecond anneal (mSA), a solid phase epitaxial regrowth (SPER), a flash anneal, a single-step anneal (SSA), a microsecond anneal (uSSA), a flash lamp anneal (FLA), and/or other suitable anneal process.

In an embodiment, the process parameter may be a parameter of a CVD epitaxy process. In an embodiment, the process parameter is a heating amount to be applied to a substrate (or wafer), chamber, susceptor, and/or other element of the tool or portion thereof. In an example, heating is controlled by a power of lamps in the CVD epitaxy tool. The process parameter determined from the reflectivity may be a watt amount for a lamp, an array of lamps, selective groups or zones of lamp(s) of an array, a ratio of power to applied by lamps (e.g., upper and lower), a percentage of power to be applied by one or more lamps, and/or other configurable heating elements and definition thereof. For example, a power of an upper lamp, upper lamp array, bottom lamp, bottom lamp array, spot lamp(s), and/or other heating source may be determined. In a further embodiment, a relative power (e.g., ratio) between heating sources or lamps may be determined. The power of one or more lamps may be changed before and/or during the epitaxial growth process.

Figure 9:
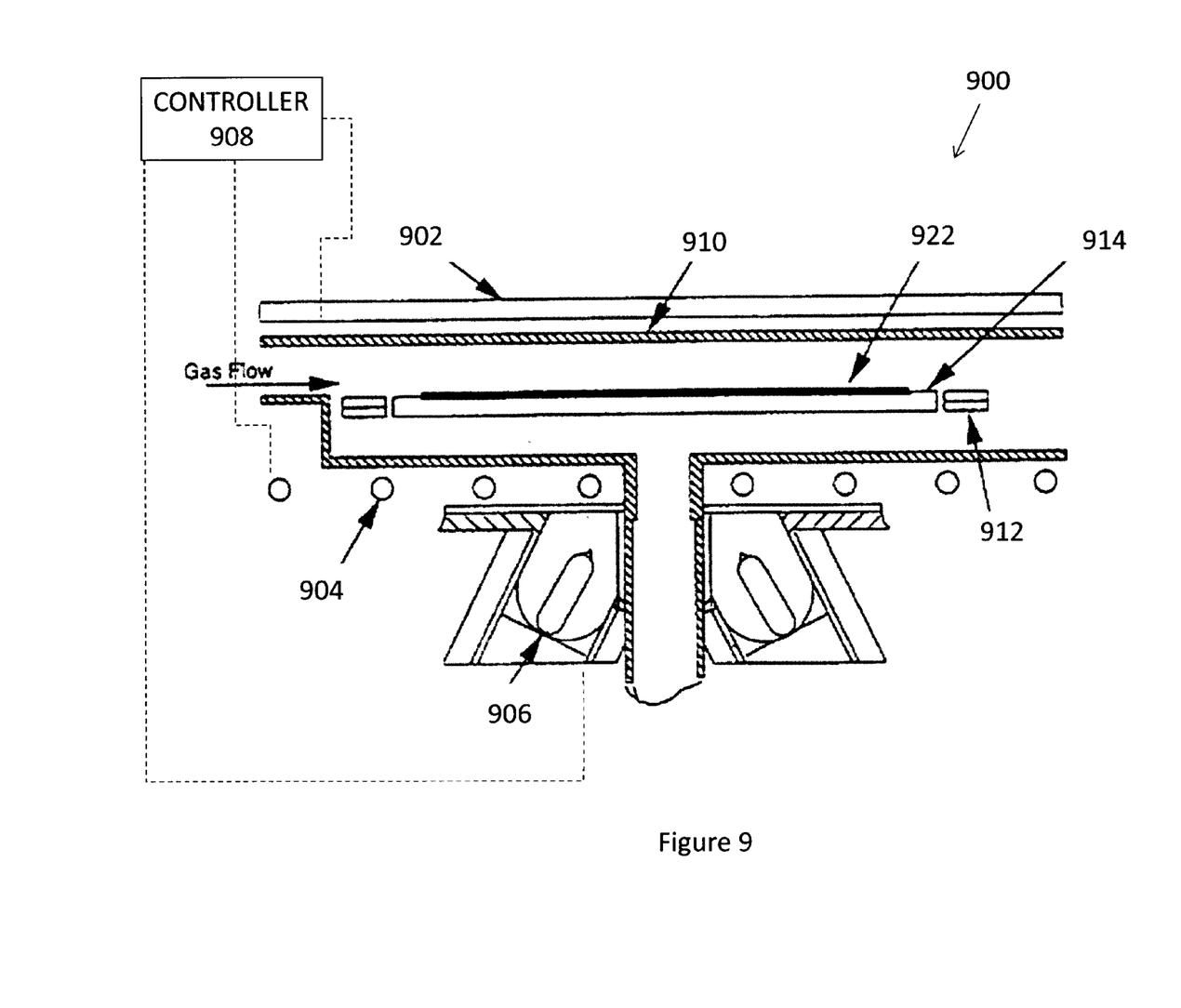
FIG. 9 is a block diagram of an embodiment of epitaxial chemical vapor deposition (CVD) tool, according to one or more aspects of the present disclosure.

In an embodiment, a CVD epitaxy tool provides a reactor section having an upper and lower array of lamps. Exemplary lamps include tungsten-halogen lamps. An exemplary power level provided by a lamp, such as an upper or lower lamp, may be approximately 6 kW. As discussed above, a percentage of the approximately 6 kW of power available may be determined using the reflectivity map, thermal map, spatial distance, or reflectivity measurement. The CVD epitaxy tool may also provide spot lamps and/or other conductive heating devices which may be similarly controlled. One exemplary CVD epitaxy tool is the Epison-1 Reactor System provided by ASM Inc., Phoenix, Ariz. However, numerous other tools are also available. FIG. 9 is illustrative of a portion of a CVD epitaxy tool 900 having an upper array of lamps 902, a lower array of lamps 904, and spot lamps 906. Each of the lamps 902, 904, 906 may be coupled to a controller 908. The tool 900 further includes a process chamber 910, susceptor rings 912, susceptor 914, and a gas flow (see FIG. 9) for performing the CVD epitaxy process using suitable parameters including those provided by the controller 908.

The controller 908 may be substantially similar to that of the computer system 700, described below with reference to FIG. 7. The controller 908 may be operable to control the power, duration, direction, and/or other configurable feature of one or more of the lamps 902, 904, and 906 according to the steps of the method 100 including block 110. The lamps 902, 904, 906 may be individually controlled, divided into sections or zones and controlled, and/or controlled as an array. It is noted that the number of lamps is exemplary only and not intended to be limiting. In an embodiment, the controller 908 uses an analysis based on the reflectivity map or reflectivity change as described above in block 106 (and continued in block 110) to determine the configuration of lamps 902, 904, and 906. For example, in an embodiment, the controller 908 provides a ratio of power between lamps 902 and 904 based on the reflectivity change of block 106. In an embodiment, the controller 908 provides a specified heating of a lamp or set of lamps of 902, 904, 906 by providing a percentage of lamp power (W) to be applied by the lamp or lamps. The upper lamps 902 may provide heating of a top surface of a wafer 922. The lower lamps 904 may provide for heating a bottom surface of a susceptor 914. The spot lamps 906 may also provide heating, such as of the bottom surface of the susceptor 914.

In an embodiment, the gas flow includes precursors suitable for forming silicon, silicon germanium, germanium, silicon carbon, and/or epitaxy materials for forming an epitaxy layer on a wafer 922 disposed in the chamber 910. The wafer 922 may be substantially similar to the wafer 200, described above with reference to FIG. 2 and/or the wafer described above in block 102 of the method 100 of FIG. 1.

The determination of the process parameter (e.g., type of anneal or CVD epitaxy parameter (e.g., power/heat) may be performed by determining a spatial distance for a given reflectivity change. This spatial distance may then be compared to the thermal diffusion length of one or more of the anneal process techniques. This comparison yields a determination if, for the given anneal, a pattern loading effect solution is may be desired to avoid and/or mitigate PLE. In an embodiment, for one or more of the anneal techniques, the respective thermal diffusion length is greater than the spatial distance for the given reflectivity change. Thus, the one or more anneal techniques that have a greater thermal diffusion length can be implemented in the process without a PLE solution (e.g., that anneal technique may be performed without accounting or otherwise correcting for PLE). In an embodiment, the given reflectivity change used to determine the spatial distance is approximately 0.1 or 10%. The anneal process selection is further discussed below.

This spatial distance may also or alternatively used to determine a parameter of the CVD epitaxy process. In an embodiment, the relationship between wafer temperature and epitaxial deposition/growth rate is determined (e.g., by modeling, experimental data) and/or received. The spatial distance may provide a determination if, for the given epitaxy process, a pattern loading effect solution may be desired to avoid and/or mitigate PLE (e.g., resultant variation in epitaxial growth). In an embodiment, the given reflectivity change used to determine the spatial distance is approximately 0.1 or 10%. The pattern loading effect solution may include determining and/or modifying a lamp power such as described herein for example to provide a more uniform heating of the wafer and resultant epitaxial growth on the wafer.

In an embodiment, the higher the reflectivity as illustrated by the reflectivity measurements and/or reflectivity map, the greater amount of the radiation energy of the heat source of the epitaxial growth process tool may be reflected from the target substrate or wafer during the process. In an embodiment, the heating is controlled by the proportion of power of lamp arrays. As but one example, in a portion of the target substrate providing higher range of reflectivity distribution (greater spatial distance), the heat absorption efficiency of substrate is of greater range within the target substrate. Thus, less/decreased power relative to the upper lamps 902 is preferred to reduce pattern loading effect (PLE). Similarly, in a portion of the target substrate providing lower range of reflectivity distribution (lower spatial distance), higher/increased power relative to the upper lamps 902 may be provided owing to less pattern loading effect concern.

Figure 6:
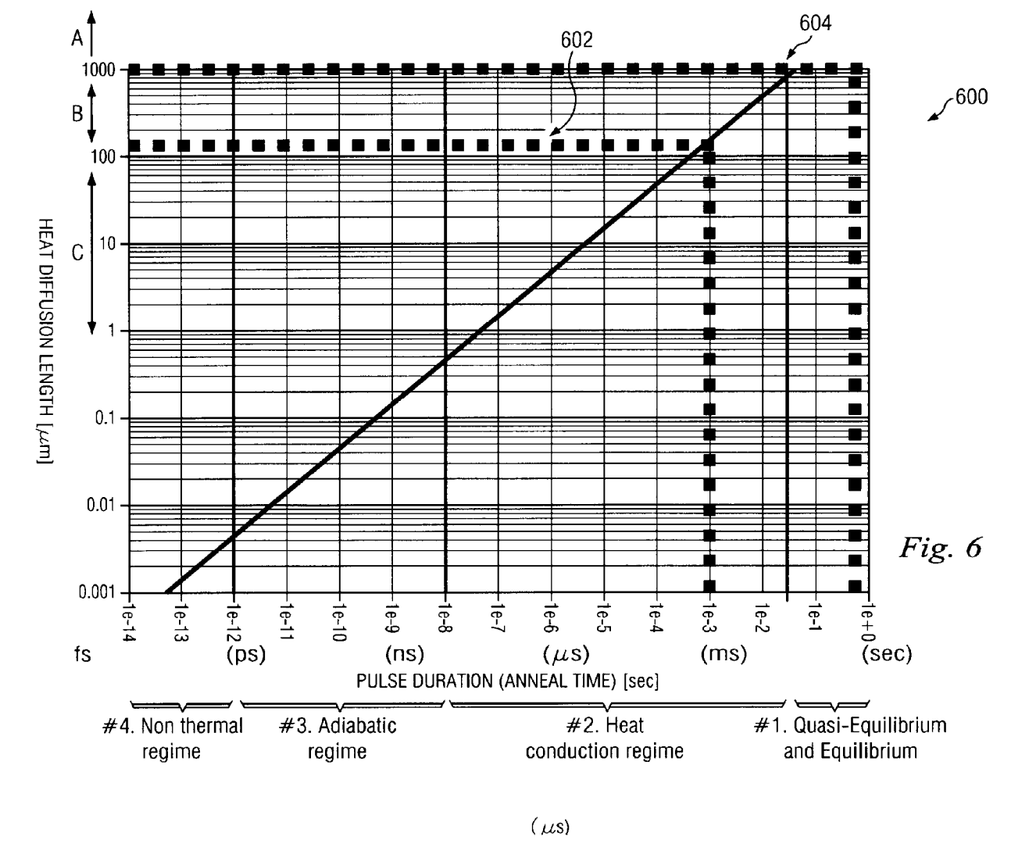
FIG. 6 is a graph illustrating an embodiment of a relationship between pulse duration of an anneal process and a heat diffusion length.

Referring again to the selection of the appeal process, FIG. 6 illustrates a graph 600 providing a semiconductor heating regime. Further description of the graph 600 may be provided in the article P. J. Timans: "A short history of pattern effects in thermal processing," Materials Science Forum Vols. 573-574 (2008) p. 355-374, which is hereby incorporated by reference in its entirety. The graph 600 has an x-axis of pulse duration (anneal time) in seconds. The graph 600 has a y-axis of heat diffusion length in microns (μm). As described above, for different anneal process techniques, there are different heat diffusion lengths. The graph 600 is illustrative of this principle. For example, the line 602 illustrates a millisecond anneal (mSA) process. The line 604 illustrates a rapid thermal anneal (RTA) process. The graph 600 may be used to determine when a given anneal process will affect the pattern loading effect of the die. In an embodiment, the duration of the anneal process is located on the x-axis and the thermal diffusion length is located on the y-axis for a given anneal process.

In an embodiment, the reflective variation is greater than or equal to 0.1 within a spatial distance of greater than or equal to 1 mm as determined from the reflectivity measurement and/or reflectivity map of the substrate. This provides a spatial distance in region A of the y-axis of graph 600 (greater than 1000 μm). Thus, in the embodiment, the loading effect will be observed on a micro second anneal, a millisecond flash anneal, a second RTA spike anneal, and any other anneal process having a thermal diffusion length less than region A. In other words, for all anneal processes having a heat diffusion length less than the spatial distance there will be a PLE. Thus, for each of those anneal types, if implemented in the process, implementation of a PLE solution or correction may be desired to avoid and/or mitigate PLE. A PLE solution or correction may include modifications in design (e.g., layout), performance criteria, or modifications of fabrication steps.

In an embodiment, the reflective variation is greater than or equal to 0.1 within a spatial distance between 200 μm and 1 mm as determined from the reflectivity measurement and/or reflectivity map of the substrate. This provides a spatial distance in region B of the y-axis of graph 600 (between 200 μm and 1000 μm). In the embodiment, the loading effect will be observed on a micro second anneal, a millisecond flash anneal, and/or any other anneal process having a thermal diffusion length less than region B. Thus, for each of those anneal types, if implemented in the process, implementation of a PLE solution or correction may be desired to avoid and/or mitigate PLE. In other words, for all anneal processes having a heat diffusion length less than the spatial distance there will be a PLE for which to account. For those anneal types, if implemented in the process, implementation of a PLE solution or correction may be desired to avoid and/or mitigate PLE. In contrast, other anneal types having a larger thermal diffusion length (e.g., a second RTA spike anneal), PLE may not be of concern. In other words, those anneals may be implemented without corrective action.

In an embodiment, the reflective variation is greater than or equal to 0.1 within a spatial distance between 1 μm and 200 μm as determined from the reflectivity measurement and/or reflectivity map of the substrate. This provides a spatial distance in region C of the y-axis of graph 600 (between 1 μm and 200 μm). In the embodiment, the loading effect will be observed on a micro second anneal and/or any other anneal process having a thermal diffusion length less than region C. Thus, for those anneal types, if implemented in the process, implementation of a PLE solution or correction may be desired to avoid and/or mitigate PLE. In other words, for all anneal processes having a heat diffusion length less than the spatial distance there will be a PLE for which to account. In contrast, other anneal types having a larger thermal diffusion length (e.g., a second RTA spike anneal, millisecond flash anneal) may be implemented without necessity of correcting or otherwise addressing PLE.

Thus, the block 110 may include a determination of when an anneal process or anneal process parameter will affect the pattern loading effects of a die or substrate. This determination may include calculating a spatial distance for a given percentage change in reflectivity and comparing this spatial distance to a heat diffusion length associated with the anneal process. A determination can then be made whether the pattern loading effect will be an issue, or not in the process. This may provide for a mechanism by which a determination is made as to what process and/or process parameter to use in the fabrication of the substrate or dies of the same or substantially similar design.

As discussed above, in an embodiment, the block 110 may alternatively or additionally include a determination of the process parameter with reference to an epitaxial growth process (e.g., CVD epitaxy). The determination may be performed by using the reflectivity measurements, reflectivity map, and/or the determined spatial distance for a given reflectivity change. In an embodiment, the given reflectivity change used to determine the spatial distance is approximately 0.1 or 10%. This spatial distance is then used to determine a heating requirement to provide a desired temperature at various regions on the target substrate and thus, desired epitaxial thickness and thickness variation across a wafer or portion thereof. Specifically, this spatial distance may yield a determination to apply a pattern loading effect solution to mitigate differences in epitaxial growth that may occur due to pattern loading effects. In an embodiment, the pattern loading effect solution includes determining/modifying one or more of the power settings for a lamp of the epitaxial tool to provide a desired epitaxial growth/epitaxial growth variation across a wafer. In a further embodiment, the pattern loading effect solution includes determining/modifying a ratio of power settings for lamps of an epitaxial tool, for example, the ratio of heating from an upper to lower array of lamps as discussed above.

In an embodiment, the block 110 further includes, or alternatively includes, a characterization of the design and/ or layout or one or more die on the wafer. The determination associated with the design may include an acceptance of a layout, a determination to modify the layout (e.g., to improve pattern loading effects), a determination to change a material type used in the die, a determination to add a material type or layer, and/or suitable design considerations.

In an embodiment, the block 110 includes a characterization of a device performance parameter associated with one or more die on the substrate. In an embodiment, one or more of the reflectivity map and the thermal map are used to determine (e.g., predict) the device performance parameter(s). In an embodiment, the reflectivity map and/or the thermal map are used to generate a device performance parameter map. The device performance parameter map may be generated using modeling, experimental data, and/or other analysis techniques. The device performance parameter may provide a map of a relative and/or specific value for a given performance parameter of a semiconductor device such as, for example, leakage, speed, delay, and/or other performance metric.

Figure 5:
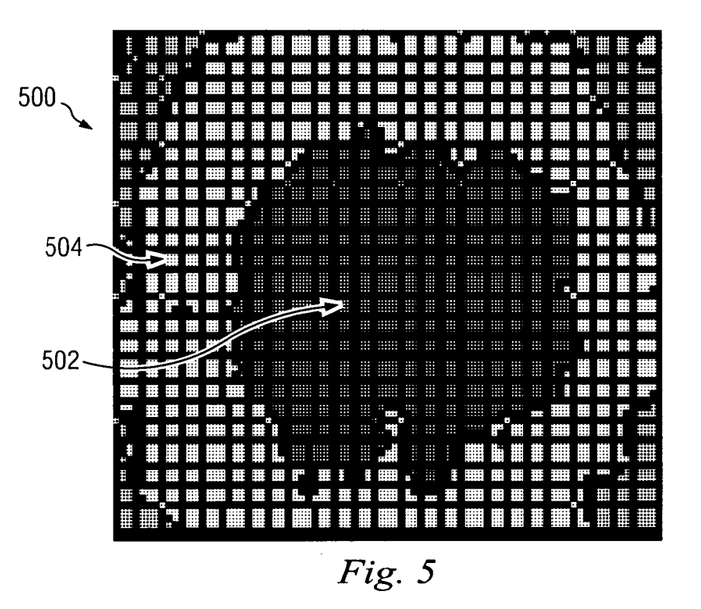
FIG. 5 is an embodiment of a device parameter map, which may be generated in one or more embodiments of the method of FIG. 1.

Referring to the example of FIG. 5, a device performance parameter map 500 is illustrated. The device performance parameter map 500 may be a circuit speed delay map. The device performance parameter map 500 includes a center-region 502 and an edge region 504. The device performance parameter map illustrates a center-slow, edge-fast profile for the associated wafer. In an embodiment, the device performance parameter map 500 may correspond with the thermal map 400, which has a center-hot, edge-cool region. In an embodiment, the device performance parameter map 500 may correspond with the reflectivity map 300, which has a center-low reflectivity, edge-high reflectivity region.

As described above, in block 110 one or more of a process parameter, design, and/or performance parameter characterization for the wafer and/or associated die is determined from at least one of the reflectivity measurement, the reflectivity map, and the thermal map. In an embodiment, the characterization is determined for all wafers having the associated die design. For example, the method 100 may be performed once to characterize a design and/or die and process, design, or performance parameter determinations made may be applied to all the associated die/design.

Thus, the method 100 provides for determination of a suitable process parameters or techniques (e.g., an anneal technique or a suitable anneal process parameter, and/or heating characteristic of a CVD epitaxy) for a given wafer and/or associated design/die. The method 100 may also and/or alternatively provide an analysis of a design (e.g., layout) associated with the wafer, for example, a determination if a desire to mitigate or otherwise account for a pattern loading effect may be provided for by a design change. The method 100 may also or alternatively provide for a determination (e.g., prediction) of a device performance parameter. The characterization of the method 100 may determine whether design changes are required, or the pattern loading effects are not of specific concern. In embodiments, the method 100 may continue to perform subsequent fabrication process including those typical of a CMOS fabrication process. Subsequent processing of the substrate provided in the method 100 may include, for example, forming an inter-layer dielectric (ILD), contacts, inter-metal dielectric (IMD) layers, metallization layers, packaging, and the like.

Figure 7:
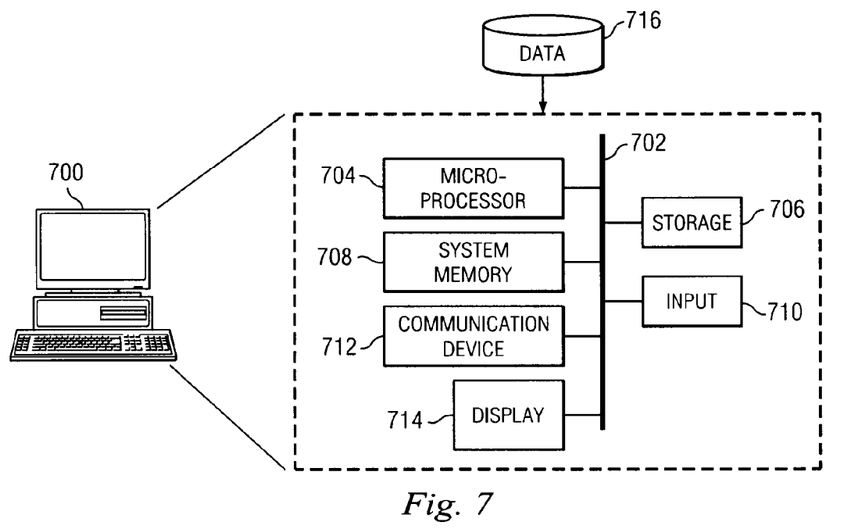
FIG. 7 is a block diagram of an embodiment of a computer system operable to perform one or more steps of the method of FIG. 1.

Referring now to FIG. 7, illustrated is an embodiment of a computer system 700 for implementing embodiments of the present disclosure including the systems and methods described herein. In an embodiment, the computer system 700 includes functionality providing for generation of a reflectivity map, a thermal map, analysis of a reflectivity map, analysis of a thermal map, determination of a process parameter, determination of a design parameter (e.g., layout, material, etc), determination of a concern of a PLE, determination and/or prediction of a device performance parameter (e.g., generation of a device performance parameter) including as described in the method 100 of FIG. 1.

The computer system 700 includes a microprocessor 704, an input device 710, a storage device 706, a system memory 708, a display 714, and a communication device 712 all interconnected by one or more buses 702. The storage device 706 may be a floppy drive, hard drive, CD-ROM, optical device or any other storage device. In addition, the storage device 706 may be capable of receiving a floppy disk, CD-ROM, DVD-ROM, or any other form of computer-readable medium that may contain computer-executable instructions. The communications device 712 may be a modem, a network card, or any other device to enable the computer system to communicate with other nodes. It is understood that any computer system 700 could represent a plurality of interconnected computer systems such as, personal computers, mainframes, PDAs, and telephonic devices. The communications device 712 may allow communications between the computer system 700 and one or more tools or computer systems used in the fabrication and/or testing of an IC.

The computer system 700 includes hardware capable of executing machine-readable instructions as well as the software for executing acts (typically machine-readable instructions) that produce a desired result. Software includes any machine code stored in any memory medium, such as RAM or ROM, and machine code stored on other storage devices (such as floppy disks, flash memory, or a CD ROM, for example). Software may include source or object code, for example. In addition, software encompasses any set of instructions capable of being executed in a client machine or server. Any combination of hardware and software may comprise a computer system. The codes, executed by a computer, may include code for generating reflectivity maps, generating thermal maps, generating process parameter maps, and/or other functionality of the method 100.

Computer readable mediums include passive data storage, such as RAM as well as semi-permanent data storage such as a compact disk read only memory (CD-ROM). In an embodiment of the present disclosure may be embodied in the RAM of a computer to transform a standard computer into a new specific computing machine. Data structures are defined organizations of data that may enable an embodiment of the present disclosure. For example, a data structure may provide an organization of data, or an organization of executable code. Data signals could be carried across transmission mediums and store and transport various data structures, and thus, may be used to transport an embodiment of the present disclosure. The microprocessor 704 may perform the correlation analysis described herein.

The display 714 may be operable to display, in human readable form, for example, the reflectivity map, the thermal map, and/or the device performance parameter map such as exemplified in FIGS. 3, 4, and 5, respectively. A database 716 may be any standard or proprietary database software known in the art. The physical location of the database 716 is not limiting and may exist remotely from the server, be accessible by internet or intranet. The disclosure of the database 716 includes embodiments that include a plurality of databases. The database 716 may include design and/or manufacturing data.

Figure 8:
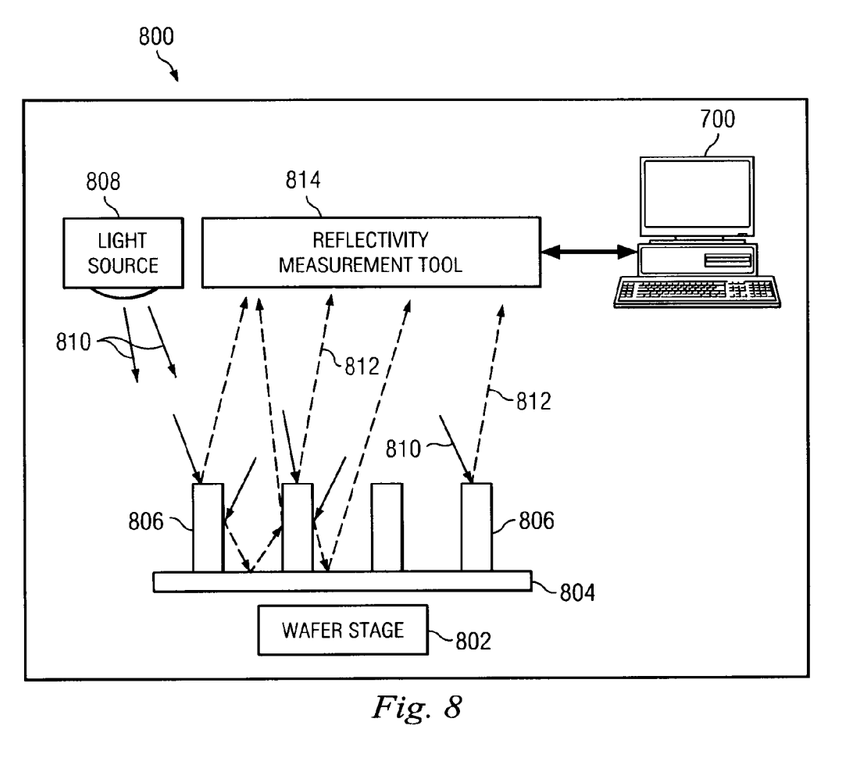
FIG. 8 is a block diagram of a system according to one or more aspects of the present disclosure.

FIG. 8 is a block diagram illustrative of a system 800 that may be used to perform one or more steps of the method 100. The system 800 includes a wafer stage 802 operable to hold a substrate, such as a wafer 804. The wafer may be substantially similar to the wafer described above with reference to block 102 of the method 100 of FIG. 1 and/or the wafer 200, described above with reference to FIG. 2. The wafer 804 includes a pattern 806 formed thereon.

The system 800 further includes a light source 808. The light source 808 may be a source having a relativity short wavelength, such as, for example, a source providing a radiation beam having a wavelength between approximately 200 nanometers (nm) and approximately 750 nm. In an embodiment, a flash Xeon lamp may be used as the light source 808. In an embodiment, the wavelength of the light source 808 is between approximately 300 nm and approximately 500 nm. A spot size of approximately 3 µm may be used. A stepping distance of approximately 50 µm or greater may be used. These parameters are by way of example. The light source 808 provides a radiation 810 directed towards the wafer 804. A portion of the radiation 810 is reflected by the wafer 804, denoted as reflected radiation 812. The amount (e.g., intensity) reflected is dependent upon the pattern 806. One of the light source 808 and the wafer stage 802 may provide for the radiation to be scanned across the substrate.

The system 800 further includes a reflectivity measurement tool 814. The reflectivity measurement tool 814 may provide any means of measuring and/or storing a reflectivity value. The reflectivity value may be determined by the amount of reflected radiation 812. The value determined by the reflectivity measurement tool 814 may be provided to a computer system, such as the computer system 700, described above with reference to FIG. 7.

In summary, the methods and systems disclosed herein provide for thermal induced intra-die (and inter-die) variation characterization. The characterization may include analysis and/or determinations associated with a design, a process parameter, and/or a device performance parameter. For example, the analysis and/or determination may include generation of thermal maps, generation of device performance parameter maps, determination of acceptability of a design/layout within a given tolerance, determination of a type of anneal process to implement in fabricating devices, and/or other suitable analysis and/or determinations discussed herein. In doing so, various embodiments of the present disclosure may offer several advantages over prior art devices. Advantages of some embodiments of the present disclosure include determination of a design and/or device performance parameters prior to performing an anneal and characterization of a die layout such that it may be used to make processing decisions in subsequent fabrication. Another advantage of an embodiment is that the method and/or system provided may be universal, for example, applicable to various different designs, various different technology nodes, etc. Further, embodiments provide for characterization of on-die variation with a resolution that is smaller than the thermal diffusion length of an anneal process. For example, in an embodiment, the resolution obtained may be 50 µm, which is smaller than the millisecond anneal (mSA) thermal diffusion length. Thus, it is possible to determine and/or resolve mSA induced loading effects. It is understood that different embodiments disclosed herein offer different disclosure, and that one of ordinary skill may make various changes, substitutions and alterations herein without departing from the spirit and scope of the present disclosure.

Advantages of some embodiments may also include allowing for compensation for pattern loading effects of a given design or wafer during an epitaxial growth process. By understanding the pattern loading effects, the power of heat sources may be adjusted to compensate for uneven epitaxy growth caused by uneven heating due to pattern loading effects.

Thus, in an embodiment provided is a method includes receiving a plurality of reflectivity measurements on a semiconductor wafer. A reflectivity map is generated based on the received plurality of reflectivity measurements. The generated reflectivity map is used to determine a process parameter of an epitaxial growth process using the reflectivity map.

In a further embodiment, the process parameter is a power setting for a lamp of a tool performing the epitaxial growth process. The lamp may be an upper lamp or a lower lamp. In an embodiment, the method includes modifying a power ratio of a first lamp and a second lamp of a chamber based on the determined process parameter. In an embodiment, a device performance parameter map may be generated from the reflectivity map. The method may also include performing the epitaxial process using the determined process parameter.

Also provided is a system including a non-transitory, computer-readable medium that stores a plurality of instructions for execution by at least one computer processor. The instructions may include those to receive a plurality of reflectivity amounts associated with a semiconductor wafer. A spatial distance may then be determined for a selected reflectivity change (e.g., 10%) using the plurality of reflectivity amounts. The spatial distance defines a distance across the semiconductor wafer within which the selected reflectivity change occurs. The spatial distance can be used to identify a pattern loading effect. A process parameter for an epitaxial growth process can be selected to compensate for the identified pattern loading effect. It is noted that without compensation, in some embodiments, the epitaxial growth process may provide uniformity issues due to the pattern loading effect.

In some embodiments, the instructions further include sending the selected process parameter to a controller associated with a chemical vapor deposition (CVD) tool. In an embodiment, the selected process parameter is a power of a lamp of a chemical vapor deposition (CVD) tool. In an embodiment, the instructions also include those to determine a first type of anneal to be performed using the determined spatial distance. In an embodiment, determining the type of anneal includes comparing the spatial distance with a thermal diffusion length associated with a first type of anneal process technique and determining that the thermal diffusion length of the first type of anneal process technique is greater than the spatial distance.

In an embodiment, the instructions include those to generate a process parameter map from the plurality of reflectivity amounts. In an embodiment, the instructions include those to generate the process parameter map include predicting of a speed of a semiconductor device.

Also provided is a system. The system may include a wafer stage suitable for holding a semiconductor wafer and a light source suitable for delivering a radiation beam to the semiconductor wafer disposed in the wafer stage. The system may also include a reflectivity measurement tool suitable for measuring a plurality of reflectivity measurements of reflectivity of the radiation beam from the light source after the radiation beam contacts various points on the semiconductor wafer. The system can further provide a non-transitory, computer-readable medium that stores a plurality of instructions for execution by at least one computer processor. The instructions provide for receiving the plurality of reflectivity measurements of from the reflectivity measurement tool and generating a reflectivity map based on the received plurality of reflectivity measurement. The instructions may also provide for receiving a reflectivity change amount (a percentage of variation of reflectivity). The instructions can then determine a spatial distance within which the received reflectivity change is provided by using the generated reflectivity map, wherein the spatial distance corresponds to a length of a surface of the semiconductor wafer. A first process is selected to perform on the semiconductor wafer based on the determined spatial distance. Additionally or alternatively, a first process parameter is also selected to perform on the semiconductor wafer using the generated reflectivity map.

In the foregoing specification, specific embodiments of the disclosure have been described. However, various modifications and changes can be made by one skilled in the art without departing from the scope of the disclosed embodiments. Accordingly, the specification and figures are to be regarded in an illustrative rather than a restrictive sense, and all such modifications are intended to be included within the scope of the disclosed embodiments.

What is claimed is:

1. A method, comprising:
   receiving a plurality of reflectivity amounts associated with a semiconductor wafer;
   determining a spatial distance for a selected reflectivity change using the plurality of reflectivity amounts, wherein the spatial distance defines a distance across the semiconductor wafer within which the selected reflectivity change occurs;
   generating a reflectivity map based on the plurality of reflectivity measurements; and
   using the generated reflectivity map to determine a process parameter of an epitaxial growth process.

2. The method of claim 1, wherein the determining the process parameter includes providing a power setting for a lamp of a tool performing the epitaxial growth process.

3. The method of claim 2, wherein the providing the power setting includes a power setting for one of an upper lamp and a lower lamp of the tool.

4. The method of claim 1, further comprising:
   modifying a power ratio of a first lamp and a second lamp of a chamber based on the determined process parameter.

5. The method of claim 1, further comprising:
   generating a device performance parameter map from the reflectivity map.

6. The method of claim 1, further comprising:
   performing the epitaxial process using the determined process parameter.

7. A method, comprising:
   receiving a plurality of reflectivity amounts associated with a semiconductor wafer;
   determining a spatial distance for a selected reflectivity change using the plurality of reflectivity amounts, wherein the spatial distance defines a distance across the semiconductor wafer within which the selected reflectivity change occurs;
   using the spatial distance to identify a pattern loading effect; and
   selecting a process parameter for an epitaxial growth process to compensate for the identified pattern loading effect.

8. The method of claim 7, further comprising:
   sending the selected process parameter to a controller associated with a chemical vapor deposition (CVD) tool.

9. The method of claim 7, wherein the selected process parameter is a power of a lamp of a chemical vapor deposition (CVD) tool.

10. The method of claim 7, further comprising:
    determining a first type of anneal to be performed using the determined spatial distance.

11. The method of claim 10, wherein the determining the type of anneal further comprises:
    comparing the spatial distance with a thermal diffusion length associated with a first type of anneal process technique and determining that the thermal diffusion length of the first type of anneal process technique is greater than the spatial distance.

12. The method of claim 7, further comprising:
    generating a process parameter map from the plurality of reflectivity amounts.

13. The method of claim 7, wherein the generating the process parameter map includes:
    predicting a speed of a semiconductor device.

14. A method, comprising:
    delivering a radiation beam to a semiconductor wafer using a light source;
    measuring a plurality of reflectivity measurements of reflectivity of the radiation beam after the radiation beam contacts various points on the semiconductor wafer;
    generating a reflectivity map based on the plurality of reflectivity measurements;
    determining a spatial distance within which a determined percentage of variation of reflectivity is provided by using the generated reflectivity map, wherein the spatial distance corresponds to a length of a surface of the semiconductor wafer;
    selecting a first anneal process to perform on the semiconductor wafer based on the determined spatial distance; and
    determining a first process parameter of an epitaxial process to perform on the semiconductor wafer using the generated reflectivity map.

15. The method of claim 14, wherein the selecting the first anneal process includes selecting an anneal process from one of a micro second laser anneal, a millisecond flash anneal, and a rapid thermal anneal (RTA).

16. The method of claim 14, wherein the radiation beam has a wavelength between approximately 400 nanometers (nm) and 5 microns.

17. The method of claim 16, wherein the light source has a spot size of approximately 3 microns.

18. The method of claim 14, further comprising:
    generating a device performance map associated with at least one of leakage, speed and delay performance.

19. The method of claim 14, wherein the determining the first process parameter includes determining a power of a lamp.

20. The method of claim 14, wherein the determining the first process parameter includes determining a ratio of an upper lamp power to a lower lamp power.

* * * * *